United States Patent [19]

Fest et al.

[11] Patent Number: 4,742,070
[45] Date of Patent: May 3, 1988

[54] ARYLSULPHONYL-PYRIDINEALDOXIME DERIVATIVES, USEFUL AS FUNGICIDES

[75] Inventors: Christa Fest, Wuppertal; Wilhelm Brandes, Leichlingen; Gerd Hänssler; Paul Reinecke, both of Leverkusen, all of Fed. Rep. of Germany

[73] Assignee: Bayer Aktiengesellschaft, Leverkusen,, Fed. Rep. of Germany

[21] Appl. No.: 25,238

[22] Filed: Mar. 12, 1987

[30] Foreign Application Priority Data

Mar. 13, 1986 [DE] Fed. Rep. of Germany ....... 3608383

[51] Int. Cl.$^4$ ................ A61K 31/44; C07D 213/26; C07D 213/30
[52] U.S. Cl. .................................. 514/357; 546/331
[58] Field of Search .................... 546/331; 514/357

[56] References Cited

FOREIGN PATENT DOCUMENTS 0136640 4/1985 European Pat. Off. ............ 546/331
423350 4/1967 Switzerland ........................ 546/331
651552 9/1985 Switzerland ........................ 546/331

OTHER PUBLICATIONS

Williams et al. J. Pham. Sci. 56(1967) No. 10 pp. 1354–1357

Primary Examiner—Henry R. Jiles
Assistant Examiner—J. Richter
Attorney, Agent, or Firm—Sprung Horn Kramer & Woods

[57] ABSTRACT

Arylsulphonyl-pyridinealdoxime derivatives of the formula (I)

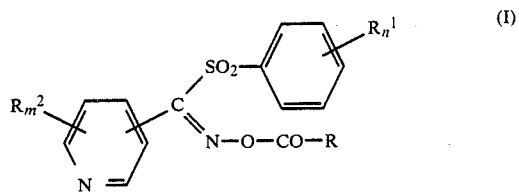

in which R, R$^1$, R$^2$, n and m have the meanings stated in the description, and their use as agents for combating pests.

The new arysulphonyl-pyridinealdoxime derivatives of the formula (I) can be prepared from suitable arylsulphonyl-pyridinealdoximes and suitable carbonyl compounds.

7 Claims, No Drawings

ARYLSULPHONYL-PYRIDINEALDOXIME DERIVATIVES, USEFUL AS FUNGICIDES

The present invention relates to new arylsulfonyl-pyridinealdoxime derivatives, a process for their preparation and their use as agents for combating pests, in particular as fungicides.

A number of aldoxime derivatives are already known. Arylsulphonylbenzaldoximes, such as α-phenylsulphonyl-2,6-dichlorobenzaldoxime, are, for example, known and their use as agents for combating pests, and above all their use in agents for combating wheat smut (cf. Swiss Patent No. 423,350). In addition, phenylpyridinealdoximes, such as, for example, phenyl-O-ethylcarbonylpyridinealdoxime, and their antihistaminic action, are known (cf. J. pharm. Sci. 56(1967) No. 10, pp. 1354–1357).

New arylsulfonyl-pyridinealdoxime derivatives of the general formula (I)

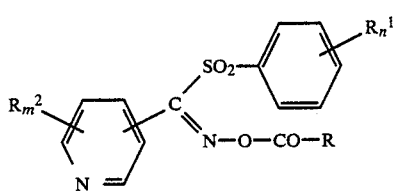

have been found, in which
R represents alkyl or alkoxy,
$R^1$ represents halogen, alkyl, alkoxy, alkylthio, halogenoalkyl, halogenoalkoxy, halogenoalkylthio, nitro, alkoxycarbonyl or alkylcarbonylamino,
$R^2$ represents halogen or alkyl,
n represents an integer 0, 1, 2, 3, 4 or 5 and
m represents an integer 0, 1, 2, 3 or 4
it being possible for the substituents in the rings to be identical or different.

It has also been found that the arylsulphonyl-pyridinealdoxime derivatives of the general formula (I)

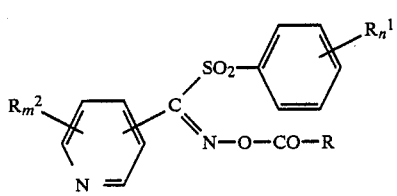

in which
R represents alkyl or alkoxy,
$R^1$ represents halogen, alkyl, alkoxy, alkylthio, halogenoalkyl, halogenoalkoxy, halogenoalkylthio, nitro, alkoxycarbonyl or alkylcarbonylamino,
$R^2$ represents halogen or alkyl,
n represents an integer 0, 1, 2, 3, 4 or 5 and
m represents an integer 0, 1, 2, 3 or 4,
it being possible for the substituents in the rings to be identical or different,
are obtained when arylsulphonyl-pyridinealdoximes of the general formula (II)

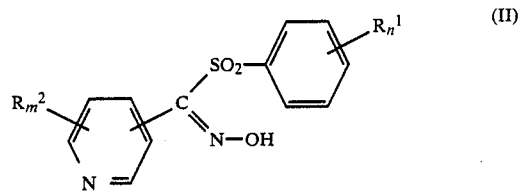

in which
$R^1$, $R^2$, n and m have the above-mentioned meanings, are reacted with carbonyl compounds of the general formula (III)

$$X-CO-R \qquad (III)$$

in which
R has the above-mentioned meanings and
X represents a halogen atom, preferably chlorine, or the radical —O—COR,
if appropriate in the presence of a solvent or diluent and if appropriate in the presence of an acid-binding agent.

The arylsulphonyl-pyridinealdoxime derivatives of the formula (I), according to the invention, exhibit powerful biological and above all fungicidal properties.

Surprisingly, the compounds according to the invention display considerably more powerful, in particular fungicidal, activity than the compounds known from the prior art which are, from the point of view of their structure and/or action, very closely related compounds.

The compounds of the formula (I), according to the invention, can be obtained as syn- or anti-isomers or as mixtures thereof of varying composition. The invention relates both to the pure isomers and to the mixtures of isomers.

The alkyl radicals R, $R^1$ and $R^2$ and the alkyl parts in the alkoxy radicals in R and $R^1$ can be straight-chain or branched and contain preferably in each case 1 to 6, and in particular 1 to 4 carbon atoms. Examples which may be mentioned are: methyl, ethyl, n-propyl, iso-propyl, n-butyl, sec.-butyl, iso-butyl, tert.-butyl, n-pentyl, iso-pentyl, sec.-pentyl, n-hexyl, sec.-hexyl, methoxy, ethoxy, n-propoxy, iso-propoxy, n-butoxy, iso-butoxy, sec.-butoxy, tert.-butoxy, n-pentoxy, iso-pentoxy, sec.-pentoxy, n-hexoxy and sec. hexoxy.

The alkylthio radicals in $R^1$ can be straight-chain or branched and certain preferably 1 to 6, in particular 1 to 4, and particularly preferably 1 to 3 carbon atoms. Examples which may be mentioned are: methylthio, ethylthio, n-propylthio, iso-propylthio, n-butylthio, iso-butylthio, sec.-butylthio, tert.-butylthio, n-pentylthio and n-hexylthio.

The halogenoalkyl parts in $R^1$ in the radicals halogenalkyl, halogenalkoxy and halogenalkylthio contain preferably in each case 1 to 6, in particular 1 to 4 and particularly preferably 1 or 2 carbon atoms and preferably 1 to 9, in particular 1 to 5, and particularly preferably 1 to 4 identical or different halogen atoms. Examples which may be mentioned are: trichlormethyl, trifluormethyl, dichlorfluoromethyl, trichloroethyl, tetrachloroethyl, trichloromethoxy, trichloroethoxy, tetrachloroethoxy, trichloromethylthio, trifluoromethylthio, dichlorofluoromethylthio, trichloroethylthio and tetrachloroethylthio.

Halogen in $R^1$ and $R^2$, as well as in the radicals such as halogenoalkyl, denotes fluorine, chlorine, bromine or iodine, in particular fluorine or chlorine, unless particularly defined elsewhere.

Alkoxycarbonyl and alkylcarbonylamino in $R^1$ contain in each case in the alkyl parts preferably 1 to 4, in particular 1 to 3 carbon atoms, and particularly preferably 1 or 2 carbon atoms. Examples which may be mentioned are: methoxycarbonyl, ethoxycarbonyl, n-propoxycarbonyl, iso-propoxycarbonyl, n-butoxycarbonyl, sec.-butoxycarbonyl, iso-butoxycarbonyl, tert.-butoxycarbonyl, methylcarbonylamino, ethylcarbonylamino, n-propylcrbonylamino, iso-propylcarbonylamino, n-butylcarbonylamino, iso-butylcarbonylamino, tert.-butylcarbonylamino and tert.-butylcarbonylamino.

n preferably denotes 0, 1, 2, 3 or 4, in particular 0, 1, 2 or 3, and m preferably denotes 0, 1, 2 or 3, in particular 0 or 1.

The arylsulphonyl-pyridinealdoxime derivatives are generally defined by the formula (I).

Compounds of the formula (I) are preferred in which

R represents straight-chain or branched alkyl with 1 to 6 carbon atoms or straight-chain or branched alkoxy with 1 to 6 carbon atoms, $R^1$ represents halogen, alkyl or alkoxy with in each case 1 to 6 carbon atoms, alkylthio with 1 to 6 carbon atoms, halogenoalkyl, halogenoalkoxy or halogenoalkylthio with in each case 1 to 6 carbon atoms and in each case 1 to 9 identical or different halogen atoms, nitro, alkoxycarbonyl or alkylcarbonylamino with 1 to 4 carbon atoms in the alkoxy or alkyl part, $R^2$ represents halogen or alkyl with 1 to 6 carbon atoms, n represents an integer 0, 1, 2, 3 or 4 and m represents an integer 0, 1, 2 or 3.

Compounds of the formula (I) in which

R represents straight-chain or branched alkyl with 1 to 4 carbon atoms or straight-chain or branched alkoxy with 1 to 4 carbon atoms, $R^1$ represents halogen, straight-chain or branched alkyl with 1 to 4 carbon atoms, straight-chain or branched alkoxy with 1 to 4 carbon atoms, straight-chain or branched alkylthio with 1 to 4 carbon atoms, halogenoalkyl with 1 to 4 carbon atoms and 1 to 5 identical or different halogen atoms, halogenoalkoxy or halogenoalkylthio with in each case 1 to 4 carbon atoms and in each case 1 to 5 identical or different halogen atoms, nitro, straight-chain or branched alkoxycarbonyl with 1 to 3 carbon atoms or alkylcarbonylamino with 1 to 3 carbon atoms in the alkyl part, $R^2$ represents halogen or straight-chain or branched alkyl with 1 to 4 carbon atoms, n represents an integer 0, 1, 2, 3 or 4 and m represents an integer 0, 1, 2 or 3, are particularly preferred.

In particular compounds of the formula (I) may be mentioned in which

R represents straight-chain or branched alkyl or alkoxy with in each case 1 to 4 carbon atoms, $R^1$ represents fluorine, chlorine, straight-chain or branched alkyl or alkoxy with in each case 1 to 4 carbon atoms, straight-chain or branched alkylthio with 1 to 3 carbon atoms, halogenoalkyl, halogenoalkoxy or halogenoalkylthio with in each case 1 or 2 carbon atoms and in each case 1 to 4 identical or different fluorine and chlorine atoms, nitro, alkoxycarbonyl or alkylcarbonylamino with in each case 1 or 2 carbon atoms in the alkoxy or alkyl part, $R^2$ represents fluorine, chlorine or straight-chain or branched alkyl with 1 to 4 carbon atoms, n represents an integer 0, 1, 2, 3 or 4 and m represents an integer 0, 1, 2 or 3.

Compounds of the formula (I) in which

R represents straight-chain or branched alkyl or alkoxy with in each case 1 to 4 carbon atoms, $R^1$ represents fluorine, chlorine, methyl, elthyl, n-propyl, iso-propyl, methoxy, ethoxy, methylthio, trifluoromethyl, trifluoromethoxy, trifluoromethylthio, nitro, methoxycarbonyl, ethoxycarbonyl, methylcarbonylamino or ethylcarbonylamino, $R^2$ represents chlorine, methyl or ethyl, n represents an integer 0, 1, 2 or 3 and m represents an integer 0 or 1 may be mentioned with very particular preference.

If 4-methylphenylsulphonyl-2-pyridinealdoxime and ethyl-formate chloride are used as the starting compounds the course of the reaction of the process according to the invention can be illustrated by the following equation:

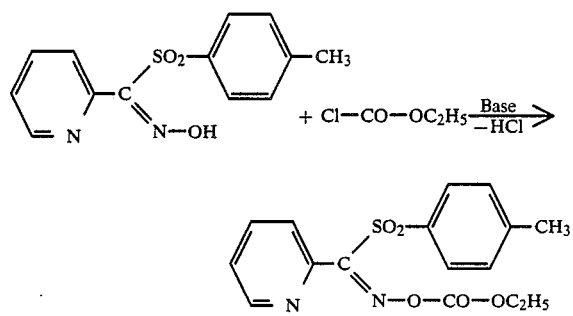

The arylsulphonyl-pyridinealdoximes required as starting compounds for carrying out the process according to the invention are defined by formula (II). These compounds are new and the subject of another application which has not yet been published. The compounds can, however, be prepared by analogous processes for example by reacting pyridinealdoximes of the formula (IV)

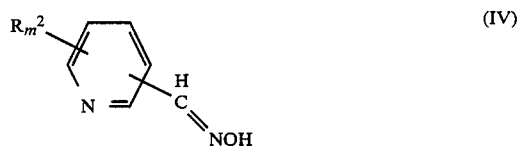

in which $R^2$ and m have the above-mentioned meanings, with chlorine, to give the corresponding α-chloropyridinealdoximes and reacting the latter with arylsulphinic acids of the formula (V)

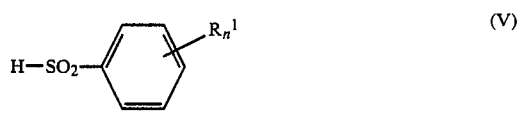

or their alkali metal compounds, in which $R^1$ and n have the above-mentioned meanings, if appropriate in the presence of a solvent or diluent, such as, for example methanol, if appropriate in the presence of a base, such as for example triethylamine and if appropriate at elevated temperatures.

The pyridinealdoximes of the formula (IV) and the arylsulphinic acids of the formula (V) are known compounds in organic chemistry.

The carbonyl compounds also required as starting compounds are defined by formula (III). They are known compounds in organic chemistry.

The process according to the invention can, if appropriate, be carried out in the presence of a solvent or diluent. In principle all inert organic solvents can be used as such. Hydrocarbons, which are optionally chlorinated, such as for example benzene, toluene, xylene, methylene chloride, chloroform, carbon tetrachloride, chlorobenzene and dichlorobenzene, as well as ethers such as diethyl and dibutyl ether, glycol dimethyl ether and diglycol dimethyl ether, tetrahydrofuran and dioxane, also ketones such as acetone, methyl ethyl, methyl isopropyl and methyl isobutyl ketone, in addition esters, such as methyl and ethyl acetate, as well as nitriles, such as for example acetonitrile and propionitrile, benzonitrile, glutaric acid nitrile, and furthermore amides, such as for example dimethyl formamide, are preferably used.

Customary inorganic or organic acid binders can be used as the acid-binding agents for the process according to the invention. Those which may be mentioned are: for example tert.-amines such as triethylamine, pyridine and triethylenediamine etc.

The reaction temperature of the process according to the invention can be varied within a relatively large temperature range. In general a temperature of between 0° C. and 120° C., preferably between 20° C. and 70° C. is used.

The reaction is normally carried out under normal pressure. When carrying out the process according to the invention the compounds of the formula (II) are generally initially introduced in a solvent with equimolar quantities of the acid binder and the carbonyl compounds of the formula (III) are added, preferably also in equimolar quantities. Working up is carried out according to generally customary methods.

A particular embodiment must also be mentioned. If X has the meaning —O—COR, which therefore means that carbocyclic acid anhydrides of the formula (III) are used, the reaction is carried out without any solvent and with a high excess of the anhydride, which then serves both as starting compound and a solvent. Working up is also carried out by customary methods.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonoadaceae, Rhizobiaceae, Enterobacteriaceae, Corynebacteriaceae and Streptomyceteae.

Some causative organisms of fungal and bacterial diseases included under the above-mentioned main headings, are mentioned below as non-limiting examples:

Xanthomonas species, such as, for example, *Xanthomonas campestris* pv. *oryzae;*

Pseudomonas species, such as, for example, *Pseudomonas syringae* pv. *lachrymans;*

Erwinia species, such as, for example, *Erwinia amylovora;* Pythium species, such as, for example, *Pythium ultimum;* Phytophthora species, such as, for example, *Phytophthora infestans;*

Pseudoperonospora species, such as, for example, *Pseudoperonospora cubensis;*

Plasmopara species, such as, for example, *Plasmopara viticola;*

Peronospora species, such as, for example, *Peronospora pisi* or *P. brassicae;*

Erysiphe species, such as, for example, *Erysiphe graminis;*

Sphaerotheca species, such as, for example, *Sphaerotheca fuliginea;*

Podosphaera species, such as, for example, *Podosphaera leucotricha;*

Venturia species, such as, for example, *Venturia inaequalis;*

Pyrenophora species, such as, for example, *Pyrenophora teres* or *P. graminea;*

(Conidial form: Drechlera, Synonym: Helminthosporium); Cochliobolus species, such as, for example, *Cochliobolus sativus;*

(Conidial form: Drechslera, Synonym: Helminthosporium); Uromyces species, such as, for example, *Uromyces appendiculatus;*

Puccinia species, such as, for example, *Puccinia recondita;*

Tilletia species, such as, for example, *Tilletia caries;*

Ustilago species, such as, for example, *Ustilago nuda* or *Ustilago avenae;*

Pellicularia species, such as, for example, *Pellicularia sasakii;*

Pyricularia species, such as, for example, *Pyricularia oryzae;*

Fusarium species, such as, for example, *Fusarium culmorum;*

Botrytis species, such as, for example, *Botrytis cinerea;*

Septoria species, such as, for example, *Septoria nodorum;*

Leptosphaeria species, such as, for example, *Leptophaeria nodorum;*

Cercospora species, such as, for example, *Cercospora canescens;*

Alternaria species, such as, for example, *Alternaria brassicae;*

Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention can be used very successfully for combating vegetable and fruit diseases, caused for example by *Venturia inaequalis* or *Botrytis cinerea*, for combating rice diseases caused, for example, by *Pyricularia oryzae* and for combating cereal diseases caused, for example, by *Puccinia condita*.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example, ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, maize, cobs and tobacco stalks. As emulsifying and/or foam-forming agents, there are suitable: for example, non-ionic and anionic emulsifiers, such as polyoxyethylene-fatty acid esters, polyoxyethylene-fatty alcohol ethers, for example alkylaryl polyglycol ethers, alkylsulphonates, alkyl-sulphates, arylsulphonates as well as albumin hydrolysation products. As dispersing agents there are suitable: for example, ligninsulphite waste liquors and methylcellulose.

Adhesives such as carboxymethylcellulose and natural and synthetic polymers in the form of powders, granules or latices, such as gum arabic, polyvinyl alcohols and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts or iron, manganese, boron, copper, cobalt, molybdenum and zinc.

The formulation in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and also as mixtures with fertilisers and other growth regulators.

The active compounds can be used as such, in the form of their formulations or as the use forms prepared therefrom, such as ready-to-luse solutions, emulsifiable concentrates, emulsions, foams, suspensions, wettable powders, pastes, soluble powders, dusting agents and granules. They are used in the customary manner, for example by watering, spraying, atomising, scattering, dusting, foaming, coating and the like. Furthermore, it is possible to apply the active compounds in accordance with the ultra-low volume process or to inject the active compound preparation or the active compound itself into the soil. It is also possible to treat the seeds of plants.

In the treatment of parts of plants, the active compound concentrations in the use forms can be varied within a substantial range. They are, in general, from 1 to 0.0001% by weight, preferably from 0.5 and 0.001%.

For the treatment of seed, amounts of active compound of 0.001 to 50 g, especially 0.01 to 10 g, are generally employed per kilogram of seed.

For the treatment of soil, active compound concentrations, at the point of action, of 0.00001 to 0.1% by weight, especially of 0.0001 to 0.02%, are generally employed.

Preparative examples

EXAMPLE 1

Initial Product

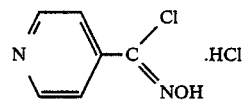

40.6 g (0.333 m) of pyridine-4-aldoxime are dissolved in 350 ml of methylene chloride and chlorine (dried) is introduced at −15° C. until saturation is reached. The reaction mixture is allowed to reach room temperature overnight and is then filtered by suction. The reaction product is washed with methylene chloride and then with acetone and is subsequently rinsed with ether. 60 g (93.4% of theory) of the required substance with a melting point of 203° C. (decomposition) are obtained.

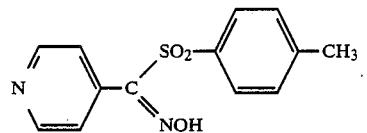

19.3 g (0.1 m) of α-chloro-pyridine-4-aldoximehydrochloride are dissolved in 250 ml of methanol and 18.7 g (0.105 m) of sodium 4-methylphenylsulphinate are added, 14 ml (0.1 m) of triethylamine are also added in order to liberate the α-chloropyridine-4-aldoxime. The reaction proceeds in a slightly exothermic manner. The reaction mixture is kept at room temperature and stirring is continued overnight at this temperature. The mixture is then poured onto about 1 l of ice water and the precipitate formed by stirring is filtered by suction, washed and dried. The reaction product is recrystallised from isopropanol. 8.1 g (29% of theory) of the required compound with a melting point of 138° C. are obtained.

End Product

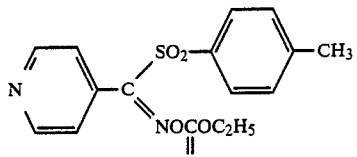

13.8 g (0.05 m) of α-(4-methylphenylsulphonyl)pyridine-4-aldoxime are dissolved in 150 ml of acetonitrile and 7 ml (0.05 m) of triethylamine and 5.5 g (0.05 m) of ethyl chloroformate are added. The reaction proceeds exothermically.

The reaction mixture is stirred overnight at room temperature and then poured onto 750 ml of water and the precipitate formed by stirring is filtered by suction, washed and dried. The reaction product is recrystallised from isopropanol. 7.4 g (43% of theory) of the required compound with a melting point of 126° C. are obtained.

The compounds of the formula (I) can be prepared according to examples 1 and 9:

$$\text{(I)}$$

| Example No. | R | $R^1$ | $R^2$ | n | m | position of the pyridine ring | Physical Data (Melting point in °C.) |
|---|---|---|---|---|---|---|---|
| 2 | —CH₃ | 4-CH₃ | — | 1 | 0 | 4 | 184 |
| 3 | —OC₂H₅ | — | — | 0 | 0 | 4 | 108 |
| 4 | —OC₂H₅ | 4-Cl | — | 1 | 0 | 4 | 129 |
| 5 | —OC₂H₅ | 4-Cl | — | 1 | 0 | 3 | 43 |
| 6 | —OC₂H₅ | — | — | 0 | 0 | 3 | 148 |
| 7 | —OC₂H₅ | 4-CH₃ | — | 1 | 0 | 3 | 133 |
| 8 | —OCH₃ | 4-CH₃ | — | 1 | 0 | 2 | 138 |

EXAMPLE 9

100 ml of acetic anhydride are added to 27.6 g (0.1 m) of α-(4-methyl-phenylsulphonyl)-pyridine-2-aldoxime and the mixture is stirred at 50° C. overnight. The reaction solution is filtered, the filtrate is evaporated in a rotary evaporator and the residue remaining is recrystallised from isopropanol. Yield: 23.2 g = 73% of theory; melting point: 88° C.

| Example No. | R | $R^1$ | $R^2$ | n | m | Position of the pyridine ring | Physical Data (Melting point in °C.) |
|---|---|---|---|---|---|---|---|
| 10 | —OC₂H₅ | 4-CH₃ | 3-CH₃ | 1 | 1 | 2 | 91 |
| 11 | —OC₂H₅ | — | 3-CH₃ | 0 | 1 | 2 | 57 |
| 12 | —OCH₃ | 4-Cl | — | 1 | 0 | 2 | 75 |
| 13 | —OC₂H₅ | 4-Cl | — | 1 | 0 | 2 | 125 |
| 14 | —OC₃H₇—i | 4-Cl | — | 1 | 0 | 2 | 82 |
| 15 | —OC₃H₇—i | 4-CH₃ | — | 1 | 0 | 3 | 133–34 |
| 16 | —OCH₃ | 4-Cl | — | 1 | 0 | 4 | 142 |
| 17 | —OCH₃ | — | — | 0 | 0 | 4 | 140 |
| 18 | —OC₄H₉—i | 4-CH₃ | — | 1 | 0 | 3 | 145 |
| 19 | —OC₂H₅ | 4-CH₃ | — | 1 | 0 | 2 | 80 |
| 20 | —OCH₃ | 4-Cl | — | 1 | 0 | 3 | 147 |
| 21 | —OC₃H₇—i | 4-CH₃ | — | 1 | 0 | 2 | 98 |
| 22 | —OCH₃ | 4-CH₃ | 3-CH₃ | 1 | 1 | 2 | 119 |
| 23 | —OCH₃ | — | 3-CH₃ | 0 | 1 | 2 | 101 |
| 24 | —OCH₃ | 4-CH₃ | — | 1 | 0 | 3 | 161 |
| 25 | —OCH₃ | — | — | 0 | 0 | 3 | 94 |
| 26 | —OC₄H₉—i | 4-CH₃ | — | 1 | 0 | 2 | 84 |
| 27 | —OC₄H₉—i | — | — | 0 | 0 | 3 | 92 |
| 28 | —OCH₃ | — | — | 0 | 0 | 2 | 113 |
| 29 | —OC₂H₅ | — | — | 0 | 0 | 2 | 92 |
| 30 | —OC₄H₉—i | — | — | 0 | 0 | 2 | 53 |
| 31 | —OCH₃ | 4-CH₃ | — | 1 | 0 | 4 | 150 |
| 32 | —OC₄H₉—i | 4-Cl | — | 1 | 0 | 2 | 95 |
| 33 | —OC₄H₉—i | 4-Cl | — | 1 | 0 | 3 | 145 |
| 34 | —OC₄H₉—i | 4-CH₃ | — | 1 | 0 | 4 | 125 |
| 35 | —OC₄H₉—i | 4-Cl | — | 1 | 0 | 4 | 112 |
| 36 | —OC₄H₉—i | — | — | 0 | 0 | 4 | 83 |
| 37 | —OC₄H₉—i | 4-CH₃ | 3-CH₃ | 1 | 1 | 2 | 100 |
| 38 | —OC₄H₉—i | — | 3-CH₃ | 0 | 1 | 2 | 86 |

-continued

| Example No. | R | R¹ | R² | n | m | Position of the pyridine ring | Physical Data (Melting point in °C.) |
|---|---|---|---|---|---|---|---|
| 39 | —OC$_3$H$_7$—i | 4-CH$_3$ | 3-CH$_3$ | 1 | 1 | 2 | |
| 40 | —OC$_3$H$_7$—i | — | — | 0 | 0 | 2 | |
| 41 | —OC$_3$H$_7$—i | — | — | 0 | 0 | 2 | |
| 42 | —OC$_3$H$_7$—i | 4-Cl | — | 1 | 0 | 3 | |
| 43 | —OC$_3$H$_7$—i | — | — | 0 | 0 | 3 | |
| 44 | —OC$_3$H$_7$—i | 4-CH$_3$ | — | 1 | 0 | 4 | |
| 45 | —OC$_3$H$_7$—i | 4-Cl | — | 1 | 0 | 4 | |
| 46 | —OC$_3$H$_7$—i | — | — | 0 | 0 | 4 | |
| 47 | —OC$_3$H$_7$—i | 4-CH$_3$ | 3-CH$_3$ | 1 | 1 | 2 | |
| 48 | —OC$_3$H$_7$—i | — | 3-CH$_3$ | 0 | 1 | 2 | |

EXAMPLE

Pyricularia test (rice)/protective

Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and th stated amount of emulsifier to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

The compounds according to the invention exhibit powerful activity at a concentration of active compound of 0.025%.

TABLE

| Active compounds | Pyricularia-Test (rice)/protective | |
|---|---|---|
| | Active compound concentration in % | Disease infestation of the untreated control in % |
| [structure: pyridine-C(=NOC(O)OCH$_3$)-SO$_2$-C$_6$H$_4$-Cl] | 0,025 | 22 |
| [structure: pyridine-C(=NOCOCH(CH$_3$)$_2$)-SO$_2$-C$_6$H$_4$-CH$_3$] | 0,025 | 11 |
| [structure: 3-methyl-pyridine-C(=NOCOCH$_3$)-SO$_2$-C$_6$H$_4$-CH$_3$] | 0,025 | 0 |
| [structure: 3-methyl-pyridine-C(=NOC(O)OCH$_3$)-SO$_2$-C$_6$H$_5$] | 0,025 | 0 |

EXAMPLE

Phytophthora test (tomato)/protective

Solvent: 4.7 parts by weight acetone
Emulsifier: 0.3 parts by weight alkylarylpolyglycolether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of Phytophthora infestans.

The plants are placed in an incubation cabin at 100% relative atmospheric humidity and at about 20° C.

Evaluation is carried out 3 days after the inoculation.

The compounds according to the invention exhibit powerful activity.

EXAMPLE

Venturia test (apple)/protective

Solvent: 4.7 parts by weight acetone
Emulsifier: 0.3 parts by weight of alkylarylpolyglycolether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (Venturia inaequalis) and then remain in an incubation cabin at 20° C. and 10% relative atmospheric humidity for 1 day.

The plants are then placed in a greenhouse at 20° C. and a relative atmospheric humidity of about 70%.

Evaluation is carried out 12 days after the inoculation.

EXAMPLE

Botrytis test (beans)/protective

Solvent: 4.7 parts by weight of acetone
Emulsifier: 0.3 parts by weight of alkylarylpolyglycolether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with Botrytis cinerea are placed on each leaf. The inoculated plants are placed in a darkened humidity chamber at 20° C. 3 days after the inoculation, the size of the infected spots on the leaves is evaluated.

The compounds according to the invention exhibit powerful activity.

We claim:

1. Arylsulphonyl-pyridinealdoxime derivatives of the formula (I)

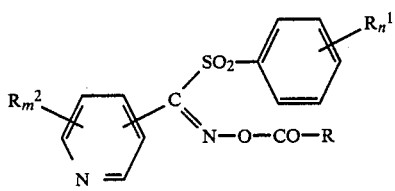

in which
R represents straight-chain or branched alkyl with 1 to 6 carbon atoms or alkoxy with 1 to 6 carbon atoms,
$R^1$ represents halogen, alkyl or alkoxy with in each case 1 to 6 carbon atoms, alkylthio with 1 to 6 carbon atoms, halogenoalkyl, halogenoalkoxy or halogenoalkylthio with in each case 1 to 6 carbon atoms and in each case 1 to 9 identical or different halogen atoms, nitro, alkoxycarbonyl or alkylcarbonylamino with 1 to 4 carbon atoms in the alkoxy or alkyl part,
$R^2$ represents halogen or alkyl with 1 to 6 carbon atoms,
n represents an integer 0, 1, 2, 3, 4 or 5 and
m represents an integer 0, 1, 2, 3 or 4.

2. Arylsulphonyl-pyridinealdoxime derivatives according to claim 1, wherein in formula (I)
n represents an integer 0, 1, 2, 3 or 4 and
m represents an integer 0, 1, 2 or 3.

3. Arylsulphonyl-pyridinealdoxime derivatives according to claim 1, wherein in the formula (I)
R represents straight-chain or branched alkyl with 1 to 4 carbon atoms or straight-chain or branched alkoxy with 1 to 4 carbon atoms,
$R^1$ represents halogen, straight-chain or branched alkyl with 1 to 4 carbon atoms, straight-chain or branched alkoxy with 1 to 4 carbon atoms, straight-chain or branched alkylthio with 1 to 4 carbon atoms, halogenoalkyl with 1 to 4 carbon atoms and 1 to 5 identical or different halogen atoms, halogenoalkoxy or halogenoalkylthio with in each case 1 to 4 carbon atoms and in each case 1 to 5 identical or different halogen atoms, nitro, straight-chain or branched alkoxycarbonyl with 1 to 3 carbon atoms or alkylcarbonylamino with 1 to 3 carbon atoms in the alkyl part,
$R^2$ represents halogen or straight-chain or branched alkyl with 1 to 4 carbon atoms,
n represents an integer 0, 1, 2, 3 or 4 and
m represents an integer 0, 1, 2 or 3.

4. Arylsulphonyl-pyridinealdoxime derivatives according to claim 1, wherein in the formula (I)
R represents straight-chain or branched alkyl or alkoxy with in each case 1 to 4 carbon atoms,
$R^1$ represents fluorine, chlorine, straight-chain or branched alkyl or alkoxy with in each case 1 to 4 carbon atoms, straight-chain or branched alkylthio with 1 to 3 carbon atoms, halogenoalkyl, halogenoalkoxy or halogenoalkylthio with in each case 1 or 2 carbon atoms and in each case 1 to 4 identical or different fluorine and chlorine atoms, nitro, alkoxycarbonyl or alkylcarbonylamino with in each case 1 o 2 carbon atoms in the alkoxy or alkyl part,
$R^2$ represents fluorine, chlorine or straight-chain or branched alkyl with 1 to 4 carbon atoms,
n represents an integer 0, 1, 2, 3 or 4 and
m represents an integer 0, 1, 2 or 3.

5. Arylsulphonylpyridinealdoxime derivatives according to claim 1, wherein in the formula (I)
R represents straight-chain or branched alkyl or alkoxy with in each case 1 to 4 carbon atoms,
$R^1$ represents fluorine, chlorine, methyl, ethyl, n-propyl, isopropyl, methoxy, ethoxy, methylthio, trifluoromethyl, trifluoromethoxy, trifluoromethylthio, nitro, methoxycarbonyl, ethoxycarbonyl, methylcarbonylamino or ethylcarbonylamino,
$R^2$ represents chlorine, methyl or ethyl,
n represents an integer 0, 1, 2 or 3 and
m represents an integer 0 or 1.

6. A fungicidal composition comprising a fungicidally effective amount of a compound according to claim 1 and a diluent.

7. A method of combating fungi which comprises applying to such fungi or to a fungus habitat of a compound according to claim 1 and a diluent.

* * * * *

UNITED STATES PATENT AND TRADEMARK OFFICE
CERTIFICATE OF CORRECTION

PATENT NO. : 4,742,070
DATED : May 3, 1988
INVENTOR(S) : Christa Fest, et al

It is certified that error appears in the above-identified patent and that said Letters Patent is hereby corrected as shown below:

Col. 4, line 8         Correct spelling of --ethyl--

Signed and Sealed this

Twenty-fourth Day of January, 1989

*Attest:*

DONALD J. QUIGG

*Attesting Officer*         *Commissioner of Patents and Trademarks*

UNITED STATES PATENT AND TRADEMARK OFFICE
CERTIFICATE OF CORRECTION

PATENT NO. : 4,742,070

DATED : May 3, 1988

INVENTOR(S) : Christa Fest, et al

It is certified that error appears in the above-identified patent and that said Letters Patent is hereby corrected as shown below:

Col. 10, line 15, last column, line 1 under heading

Delete "184" and substitute --54--

Signed and Sealed this

Second Day of January, 1990

Attest:

JEFFREY M. SAMUELS

Attesting Officer

Acting Commissioner of Patents and Trademarks